United States Patent
Wallace

(10) Patent No.: US 8,226,680 B2
(45) Date of Patent: *Jul. 24, 2012

(54) SYSTEM FOR EMBOLIZING A TARGET SITE IN A BODY BY APPLICATION OF AN EXTERNAL ENERGY

(75) Inventor: Michael P. Wallace, Pleasanton, CA (US)

(73) Assignees: Stryker Corporation, Kalamazoo, MI (US); Stryker NV Operations Limited, Dublin (IE)

(*) Notice: Subject to any disclaimer, the term of this patent is extended or adjusted under 35 U.S.C. 154(b) by 130 days.

This patent is subject to a terminal disclaimer.

(21) Appl. No.: 12/873,008

(22) Filed: Aug. 31, 2010

(65) Prior Publication Data

US 2010/0331666 A1 Dec. 30, 2010

Related U.S. Application Data

(63) Continuation of application No. 10/669,543, filed on Sep. 23, 2003, now Pat. No. 7,789,891.

(51) Int. Cl.
*A61M 29/00* (2006.01)
(52) U.S. Cl. ....... 606/200; 606/114; 606/213; 623/1.42; 128/898
(58) Field of Classification Search ........... 606/200, 606/213, 114; 623/1.42; 128/898
See application file for complete search history.

(56) References Cited

U.S. PATENT DOCUMENTS

| | | | |
|---|---|---|---|
| 4,994,069 | A | 2/1991 | Ritchart et al. |
| 5,257,635 | A | 11/1993 | Langberg |
| 5,304,194 | A | 4/1994 | Chee et al. |
| 5,405,322 | A | 4/1995 | Lennox et al. |
| 5,507,744 | A | 4/1996 | Tay et al. |
| 5,624,461 | A | 4/1997 | Mariant |
| 5,639,277 | A | 6/1997 | Mariant et al. |

(Continued)

FOREIGN PATENT DOCUMENTS

JP 07018357 1/1995

(Continued)

OTHER PUBLICATIONS

Papers from file history for related application U.S. Appl. No. 10/669,203, Inventor Michael P. Wallace et al., filed Sep. 23, 2003, including (58 pages total): Non-Final Rejection for U.S. Appl. No. 10/669,203, mailed Mar. 5, 2009. Appeal Brief for U.S. Appl. No. 10/669,203, submitted Dec. 2, 2008. Final Rejection for U.S. Appl. No. 10/669,203, mailed Jun. 30, 2008. Amendment and Response to Office Action dated Jan. 9, 2008, submitted on Apr. 4, 2008. Office Action for U.S. Appl. No. 10/669,203, mailed Jan. 9, 2008.

(Continued)

*Primary Examiner* — Gary Jackson
*Assistant Examiner* — Diane Yabut
(74) *Attorney, Agent, or Firm* — Vista IP Law Group LLP

(57) ABSTRACT

A vaso-occlusive device is introduced in a cavity of a patient's vasculature, such as an aneurysm, after which an external energy source, such as a MRI machine is activated to heat the vaso-occlusive device to assist in forming a thrombus or embolism within the treatment site, to release and/or activate a diagnostic or therapeutic agent carried by the vaso-occlusive device, and/or to fuse together portions of the vaso-occlusive device to help stabilize the device in a three-dimensional shape.

13 Claims, 4 Drawing Sheets

U.S. PATENT DOCUMENTS

| | | | |
|---|---|---|---|
| 5,649,949 | A | 7/1997 | Wallace et al. |
| 5,669,931 | A | 9/1997 | Kupiecki et al. |
| 5,749,894 | A | 5/1998 | Engelson |
| 5,824,059 | A | 10/1998 | Wijay |
| 5,853,418 | A * | 12/1998 | Ken et al. .................. 606/191 |
| 5,941,888 | A | 8/1999 | Wallave et al. |
| 5,944,733 | A | 8/1999 | Engelson |
| 5,989,242 | A | 11/1999 | Saadat et al. |
| 6,019,757 | A | 2/2000 | Scheldrup |
| 6,024,754 | A | 2/2000 | Engelson |
| 6,102,917 | A | 8/2000 | Maitland et al. |
| 6,149,664 | A | 11/2000 | Kurz |
| 6,165,198 | A | 12/2000 | McGurk et al. |
| 6,187,024 | B1 | 2/2001 | Book et al. |
| 6,221,066 | B1 | 4/2001 | Ferrera et al. |
| 6,231,590 | B1 | 5/2001 | Wallace et al. |
| 6,270,495 | B1 | 8/2001 | Palermo |
| 6,277,125 | B1 | 8/2001 | Barry et al. |
| 6,280,457 | B1 | 8/2001 | Wallace et al. |
| 6,322,576 | B1 | 11/2001 | Wallace et al. |
| 6,397,107 | B1 | 5/2002 | Lee et al. |
| 6,458,127 | B1 | 10/2002 | Truckai et al. |
| 6,478,773 | B1 | 11/2002 | Gandhi et al. |
| 6,500,149 | B2 | 12/2002 | Gandhi et al. |
| 6,544,275 | B1 | 4/2003 | Teoh |
| 6,551,305 | B2 | 4/2003 | Ferrera |
| 6,605,101 | B1 | 8/2003 | Schaefer et al. |
| 6,605,111 | B2 | 8/2003 | Bose et al. |
| 6,620,152 | B2 | 9/2003 | Guglielmi |
| 6,623,493 | B2 | 9/2003 | Wallace et al. |
| 6,740,094 | B2 | 5/2004 | Maitland et al. |
| 7,182,744 | B2 | 2/2007 | Yamasaki et al. |
| 7,789,891 | B2 * | 9/2010 | Wallace .................. 606/200 |
| 2002/0138134 | A1 | 9/2002 | Kim et al. |
| 2005/0065545 | A1 | 3/2005 | Wallace et al. |

FOREIGN PATENT DOCUMENTS

| | | |
|---|---|---|
| WO | WO 00/72781 A2 | 12/2000 |
| WO | WO 02/39911 A2 | 5/2002 |
| WO | WO 02087416 | 11/2002 |

OTHER PUBLICATIONS

Papers from file history for related application U.S. Appl. No. 10/669,203, Inventor Michael P. Wallace et al., filed Sep. 23, 2003, including: Office Action dated Jan. 25, 2006 for related U.S. Appl. No. 10/669,203, filed Sep. 23, 2003; Inventor Michael P. Wallace. (13 pages) Amendment and Response to Office Action dated Jan. 25, 2006, submitted on May 22, 2006, for related U.S. Appl. No. 10/669,203, filed Sep. 23, 2003; Inventor Michael P. Wallace. (12 pages) Amendment and Response to Office Action dated Jan. 25, 2006, submitted on Jun. 12, 2006, for related U.S. Appl. No. 10/669,203, filed Sep. 23, 2003; Inventor Michael P. Wallace. (13 pages) Final Office Action dated Aug. 18, 2006 for related U.S. Appl. No. 10/669,203, filed Sep. 23, 2003; Inventor Michael P. Wallace. (15 pages) Amendment and Response to Final Office Action dated Aug. 18, 2006, submitted on Dec. 14, 2006, for related U.S. Appl. No. 10/669,203, filed Sep. 23, 2003; Inventor Michael P. Wallace. (21 pages) Office Action dated Jan. 9, 2007 for related U.S. Appl. No. 10/669,203, filed Sep. 23, 2003; Inventor Michael P. Wallace. (13 pages) Amendment and Response to Office Action dated Jan. 9, 2007, submitted on May 7, 2007, for related U.S. Appl. No. 10/669,203, filed Sep. 23, 2003; Inventor Michael P. Wallace. (25 pages) Final Office Action dated Jul. 25, 2007 for related U.S. Appl. No. 10/669,203, filed Sep. 23, 2003; Inventor Michael P. Wallace. (14 pages) Amendment and Response to Office Action dated Jul. 25, 2007, submitted on Oct. 25, 2007, for related U.S. Appl. No. 10/669,203, filed Sep. 23, 2003; Inventor Michael P. Wallace. (19 pages).

PCT International Search Report for PCT/US2004/029589, Applicant: Scimed Life Systems, Inc., Forms PCT/ISA/210 and 220, dated Jan. 18, 2005.

PCT Written Opinion of the International Search Authority for PCT/US2004/029589, Applicant Scimed Life Systems, Inc., Form PCT/ISA/237, dated Jan. 18, 2005.

* cited by examiner

SYSTEM FOR EMBOLIZING A TARGET SITE IN A BODY BY APPLICATION OF AN EXTERNAL ENERGY

RELATED APPLICATION DATA

The present application is a continuation of U.S. patent application Ser. No. 10/669,543, filed Sep. 23, 2003, now U.S. Pat. No. 7,789,891, the priority of which is claimed under 35 U.S.C. §120, and the contents of which are incorporated herein by reference in their entirety, as though set forth in full.

FIELD OF INVENTION

The invention relates generally to vaso-occlusive devices, and, more particularly, to applying energy from a source external to a patient's body to activate a vaso-occlusive device implanted in a body cavity of the patient.

BACKGROUND

Vaso-occlusive devices are implants that are placed in cavities, e.g., an aneurysm, blood vessel lumen, fistula, or other cavity in a patient's vasculature for the purpose of facilitating formation of an thrombus or embolism. Such vaso-occlusive devices are typically delivered by a catheter that is advanced to a treatment site endoluminally, e.g., from a percutaneous entry site, using conventional access procedures.

Well known vaso-occlusive devices include helically-wound coils that assume an elongate, "delivery" configuration when constrained within a delivery catheter, and a three-dimensional, "deployed" configuration when deployed in the body cavity and no longer constrained in the catheter. Once deployed, such vaso-occlusive devices help promote embolization and/or occlusion of the cavity. For example, vaso-occlusive devices are used to fill aneurysm cavities to reduce the risk of the further growth and/or rupture of the aneurysm.

To enhance embolization, it has been suggested to provide a coating on vaso-occlusive devices that reacts in some beneficial way (e.g., with blood) in the body. For example, U.S. Pat. No. 6,187,024 discloses vaso-occlusive devices coated with a bioactive agent and/or collagenous material. It has also been suggested to provide a coating on a vaso-occlusive device to facilitate sealing the neck of an aneurysm. For example, U.S. Pat. No. 5,749,894 discloses vaso-occlusive devices having a polymeric coating that may be melted to seal the neck of an aneurysm within which the device is deployed. The disclosed method for melting the coating, however, requires introducing an energy source, e.g., a light-emitting device, or a radio frequency ("RF") electrical energy source, into the blood vessel adjacent the aneurysm to deliver energy to heat and melt the coating.

The above-referenced U.S. Pat. Nos. 6,187,024 and 5,749,894 are each incorporated by reference herein in their entirety for all they teach and disclose.

SUMMARY

In accordance with one aspect of the invention, a vaso-occlusive device is introduced in a cavity of a patient's vasculature, such as an aneurysm, after which an external energy source, such as a MRI machine is activated to heat the vaso-occlusive device to assist in forming a thrombus or embolism within the treatment site, to release and/or activate a diagnostic or therapeutic agent carried by the vaso-occlusive device, and/or to fuse together portions of the vaso-occlusive device to help stabilize the device in a three-dimensional shape.

By way of non-limiting example, in one embodiment, the occlusive device is provided with a highly resistive ferrous material, which is heated by a variable AC magnetic field applied by an external magnetic resonance imaging ("MRI") machine. For example, the ferrous material may be embedded or otherwise carried in or by a vaso-occlusive coil, or a coating thereon.

By way of non-limiting example, heating of the occlusive device may be performed as an end in itself, i.e., to enhance the formation of a blood thrombus embolism in the cavity, or to improve the long term healing response of the thrombus and/or surrounding aneurysmal tissue, after the device is implanted. Additionally or alternatively, the increase in device temperature may cause a coating on the device to at least partially melt or soften, thereby releasing or otherwise activating a therapeutic or diagnostic agent within the cavity. Further additionally or alternatively, the heating of the device may cause the device, or portions thereof, to at least partially melt and fuse together to stabilize the vaso-occlusive device in a three-dimensional (delivery) shape in the cavity.

Other aspects and features of the invention will become apparent from consideration of the following description taken in conjunction with the accompanying drawings.

BRIEF DESCRIPTION OF THE DRAWINGS

The drawings illustrate the design and utility of preferred embodiments of the invention, in which similar elements are referred to by common reference numerals, and in which.

DETAILED DESCRIPTION OF THE ILLUSTRATED EMBODIMENTS

Figure 1A:
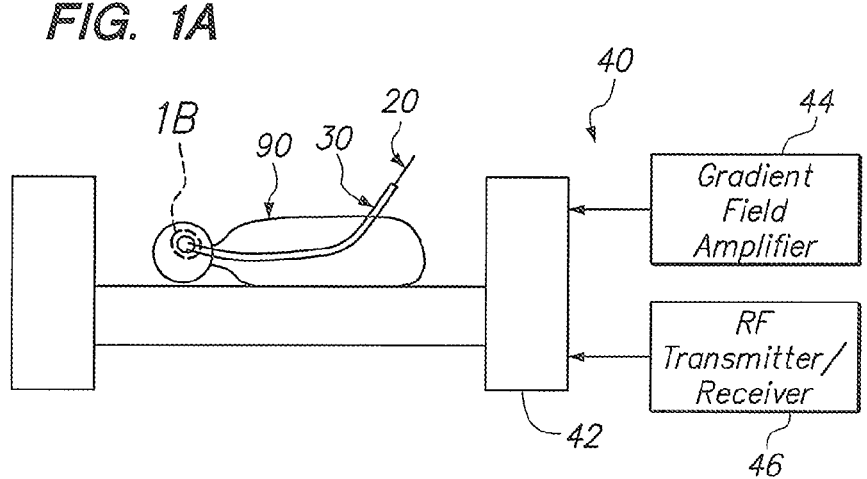
FIG. 1A is a schematic view of a system for embolizing a cavity within a patient's body, in accordance with one embodiment of the invention.
Figure 1B:
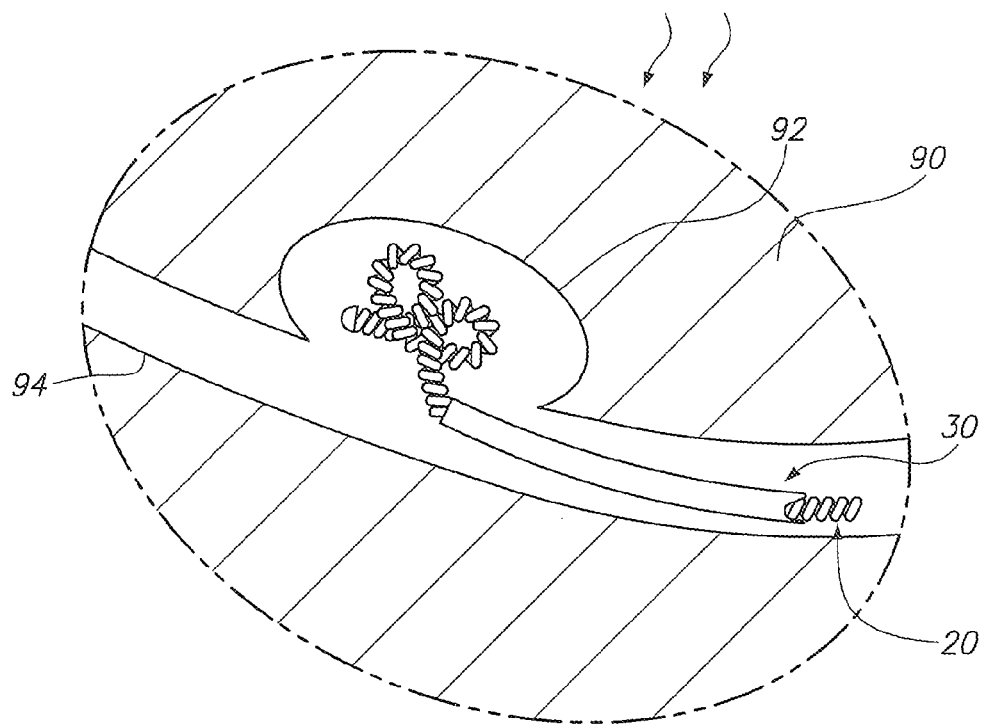
FIG. 1B is a cross-sectional detail of the patient's body, showing a vaso-occlusive device being delivered into an aneurysm.

Turning to the drawings, FIGS. 1A and 1B depict a system 10 for embolizing and/or occluding a cavity within a body 90, e.g., an aneurysm 92 extending from a blood vessel 94. Generally, the system 10 includes a vaso-occlusive device 20, a delivery catheter 30, and a magnetic resonance imaging ("MRI") machine 40.

Figure 2A:
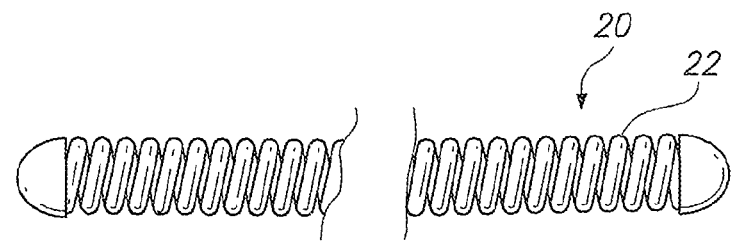
FIGS. 2A and 2B are side views of an exemplary embodiment of a vaso-occlusive device constructed in accordance with the invention.
Figure 2B:
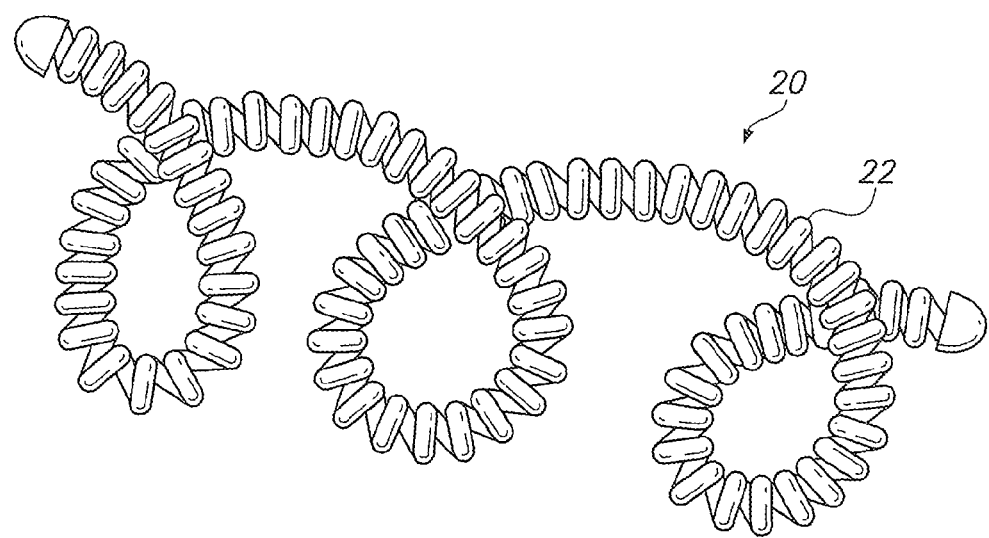

In an exemplary embodiment, such as that shown in FIGS. 2A and 2B, the vaso-occlusive device 20 includes an elongate helical coil 22 that assumes a delivery configuration (shown in FIG. 2A) when constrained in the delivery catheter 30, and a three-dimensional deployed configuration (shown in FIG. 2B) when placed in a body cavity, e.g., in aneurysm 92. The coil 22 may be formed by first winding a small, flexible wire into a linear helical form defining the delivery configuration, using known heat treatment methods. Once the delivery shape is set, the coil 22 is wound into a deployed configuration, e.g., by winding the coil 22 onto a mandrel (not shown) and heat treating the coil 22, using known methods. Thus, when the coil 22 is free from external forces, it assumes a relaxed, three-dimensional deployed configuration, as shown in FIG. 2B. It will be appreciated by those skilled in the art that the coil 22 may be biased to assume a variety of predetermined or random shapes in the deployed configuration. Alternatively, a substantially straight wire or filament, or braid of wires or filaments may be provided instead of the helical coil configuration. Additional information on methods for manufacturing vaso-occlusive devices suitable for constructing embodiments of the present invention may be found in U.S. Pat. No. 6,322,576 to Wallace et al., the disclosure of which is incorporated herein by reference for all that it teaches and discloses.

The coil 22 may be formed from a variety of materials, e.g., metals, polymers, alloys, or composites thereof. In one embodiment of the invention, described in greater detail blow, the coil 22 includes ferrous material, causing the coil 22 to be heated by activation of the MRI machine to apply a variable AC magnetic field on the device after it is implanted at a selected occlusion site in the vasculature.

In addition, the coil 22 preferably includes radiopaque material, such as metals and/or polymers. Suitable metals and alloys for the wire defining the coil 22 may include the platinum group metals, especially platinum, rhodium, palladium, and rhenium, as well as tungsten, gold, silver, tantalum, and alloys of these metals. These metals have significant radiopacity and their alloys may be tailored to accomplish an appropriate blend of flexibility and stiffness for the coil 22. They are also generally biologically inert. A platinum/tungsten alloy may be most preferred, with ferrous material mixed with or carried by the alloy. Additional suitable materials are described in the above-incorporated U.S. Pat. No. 6,322,576.

Additionally or alternatively, the coil 22 may include radiolucent fibers or polymers (or metallic threads coated with radiolucent or radiopaque fibers), such as Dacron (polyester), polyglycolic acid, polylactic acid, fluoropolymers (polytetrafluoroethylene), Nylon™ (polyamide), and/or silk. When a polymer is used as the major component of the vaso-occlusive device 20, it may be filled with some amount of radiopaque material, such as powdered tantalum, tungsten, bismuth oxide, barium sulfate, and the like. In addition, the ferrous material, e.g., iron particles, filaments and the like, may be mixed with and/or embedded in the polymer.

When the coil 22 is made from a platinum alloy or superelastic alloy, such as nitinol, or other materials, the diameter of the wire defining the coil 22 may be between about 0.0005 and 0.006 inch (0.012-0.15 mm). The wire may be wound into a primary coil having a primary diameter between about 0.005 and 0.025 inch (0.125-0.625 mm), and preferably between about 0.010 and 0.018 inch (0.25-0.45 mm). Such wire may be of an appropriate diameter to provide sufficient hoop strength to hold the vaso-occlusive device 20 in place within a chosen body cavity without distending the wall of the cavity and/or without moving substantially from the cavity as a result of the repetitive fluid pulsing experienced within the vascular system.

The axial length of the delivery configuration of the coil 22 may be between about one half and one hundred centimeters (0.5-100 cm), and preferably between about two and forty centimeters (2-40 cm). In the delivery configuration, the coil 22 may have between about ten and seventy five (10-75) turns per centimeter, and preferably between about ten and forty (10-40) turns per centimeter.

In one embodiment, a coating is provided on the coil 22, the coating having a melting temperature "$T_m$" or a glass transition temperature "$T_g$" that is less than the temperature to which the vaso-occlusive device 20 is heated by the MRI machine 40. For example, the coating may have a "$T_m$" and/or "$T_g$" of about 80-150° F. Suitable polymeric materials may include polyalkenes, polymethacrylates, polyacrylates, polyesters, polyamides, and polysaccharides. Co-polymers, blends, alloys, and block copolymers of such materials may also be used. Additional information on suitable coatings are described in the above-incorporated U.S. Pat. Nos. 5,749,894 and 6,187,024.

The coating comprises, or otherwise covers, one or more agents, e.g., a bioactive agent, a collagenous material, and/or other diagnostic or therapeutic agent(s). Exemplary bioactive agents may include genes, growth factors, biomolecules, peptides, oligonucleotides, members of the integrin family, RGD-containing sequences, oligopeptides, fibronectin, laminin, bitronectin, hyaluronic acid, silk-elastin, elastin, fibrinogen, and other basement membrane proteins with bioactive agents. By way of non-limiting example, the agent(s) may be applied in a first coating on the coil 22, with a second coating, such as the polymeric materials described above, applied to substantially cover or otherwise embed the agent(s) from exposure to the blood pool and body tissue at the deployment site in the vasculature. Alternatively, the vaso-occlusive device 20 (e.g., coil 22) may itself be formed from a polymeric material having with one or more embedded diagnostic and/or therapeutic agents that are released by heating of the device, as described in greater detail below.

In particular, one or more agent(s) may be carried on, or otherwise embedded in, the vaso-occlusive device 20 without being initially exposed or otherwise released or activated in the body upon implantation of the device. This can be advantageous, e.g., for preventing the agent(s) from release or activation if the vaso-occlusive device 20 is exposed within a blood vessel or other body region where embolization or other treatment effects are undesired. Only when the coating and/or the coil itself is heated above its melting and/or glass transition temperature, e.g., when it is determined that the implant device is placed where desired in the body cavity, are the agent(s) released or otherwise activated. For example, the agents may be prevented from making contact with the blood/tissue in the body cavity until released by the heating of the implant device (as described above). Additionally or alternatively, the agents may be exposed to the blood/tissue in the cavity, but dormant until heated (i.e., by conductive heating from the heated ferrous material) above a critical temperature threshold, activating (with the heat as the catalyst) the bioactive agent.

Returning to FIG. 1A, the MRI machine 40 includes a static field magnet 42, a gradient field amplifier 44 and a radio frequency ("RF") transmitter/receiver 46. The magnet 42 includes an internal lumen region for receiving the patient 90, and may provide a static, relatively homogeneous magnetic field over the patient 90. Alternatively, an open-MRI machine or other MR device may be used, as is well-known. During conventional operation, the gradient field amplifier 44 generates variable AC magnetic field gradients that vary the static magnetic field, and the RF transmitter 46 transmits RF pulse sequences over the patient's body to cause the patient's tissues to emit MR response signals. The MR response signals may be used to generate images of the patient's body 90, as is well-known.

When the MRI machine 40 is activated, the variable AC magnetic field generated by the magnet 42 and gradient field amplifier 44 will agitate the ferrous material in the vaso-occlusive device 20, thereby causing the ferrous material to heat. Other portions of the vaso-occlusive device 20, e.g., a coating and/or polymeric material defining the coil 22 itself, are heated by conduction from the heated ferrous material above their "$T_m$" and/or "$T_g$," causing the coating and/or polymeric material portions to at least partially melt or soften. Additionally or alternatively, heat generated by the interaction between the MRI device 40 and the ferrous material in the vaso-occlusive device 20 heats the surrounding blood or tissue to enhance embolization of the site and/or promote improved long term healing of the embolism and/or surrounding aneurysmal tissue. Notably, a coating on the occlusive device may itself include ferrous material.

More particularly, the variable AC magnetic field can heat the ferrous material through at least two mechanisms. First, the material can be heated due to hysteresis losses associated with the material being alternatively energized with positive and negative energy fields; i.e., as some materials are less efficient in responding to the alternating polarization, resulting in current losses which produce heat. Materials that are poor conductors, such as ferrous materials, produce more heat effects than highly conductive materials such as copper, platinum or aluminum. Other factors that effect hysteresis losses include the flux density and the MR frequency of the selected materials.

A second mechanism for the generation of heat involves conduction losses. The MR machine produces a conduction field around the device, thereby producing a voltage potential across the device. This voltage potential produces eddy currents in the occlusive device. Some materials and some implant device constructions are more conductive than others. Less conductive implants will result in more heat being generated. By way of example, flat ribbon material, rather than round wire stock, will increase resistance (and, thus, heating), as will using ferrous materials over conductive materials such as copper, platinum or aluminum.

Figure 3A:
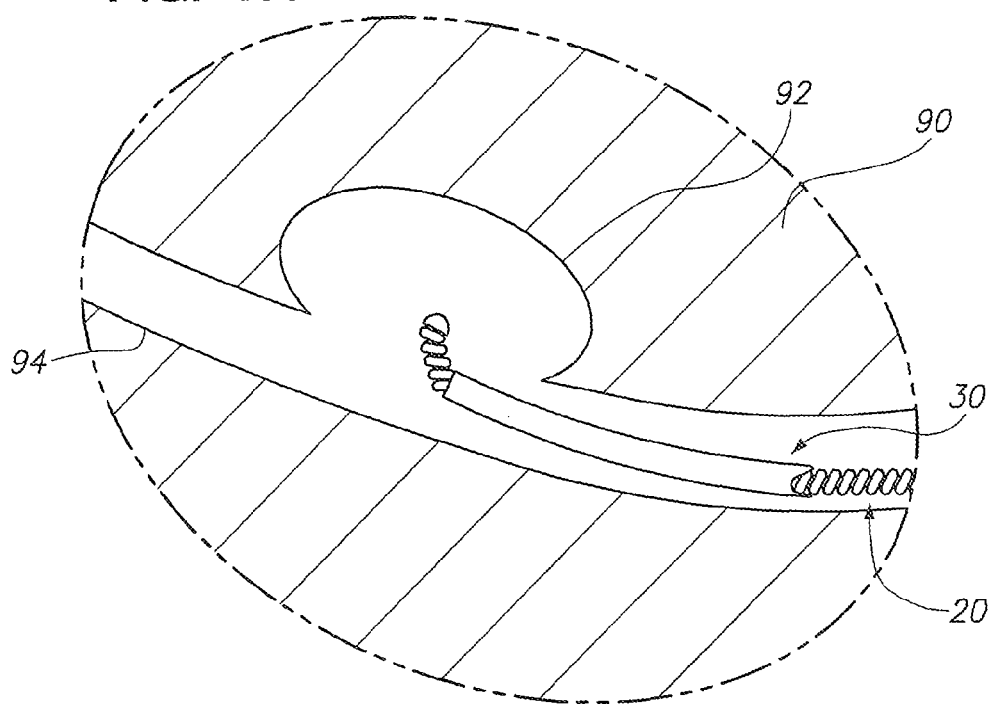
FIGS. 3A-3C are cross-sectional views of a patient's body, illustrating a method for treating an aneurysm performed in accordance with embodiments of the invention.
Figure 3B:
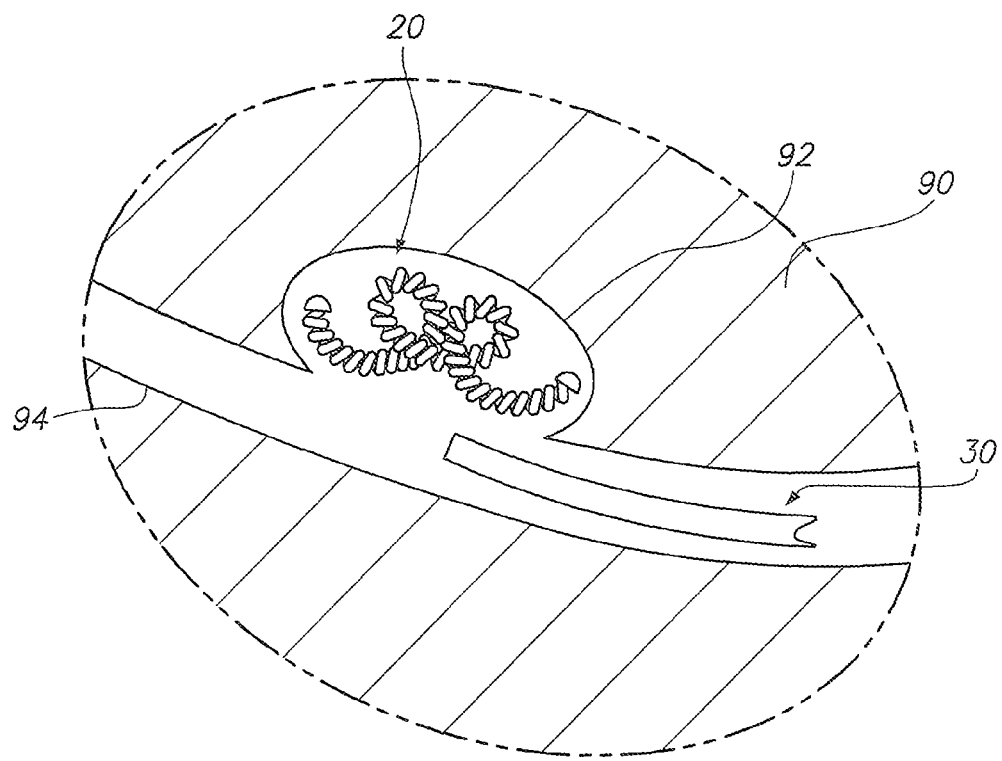
Figure 3C:
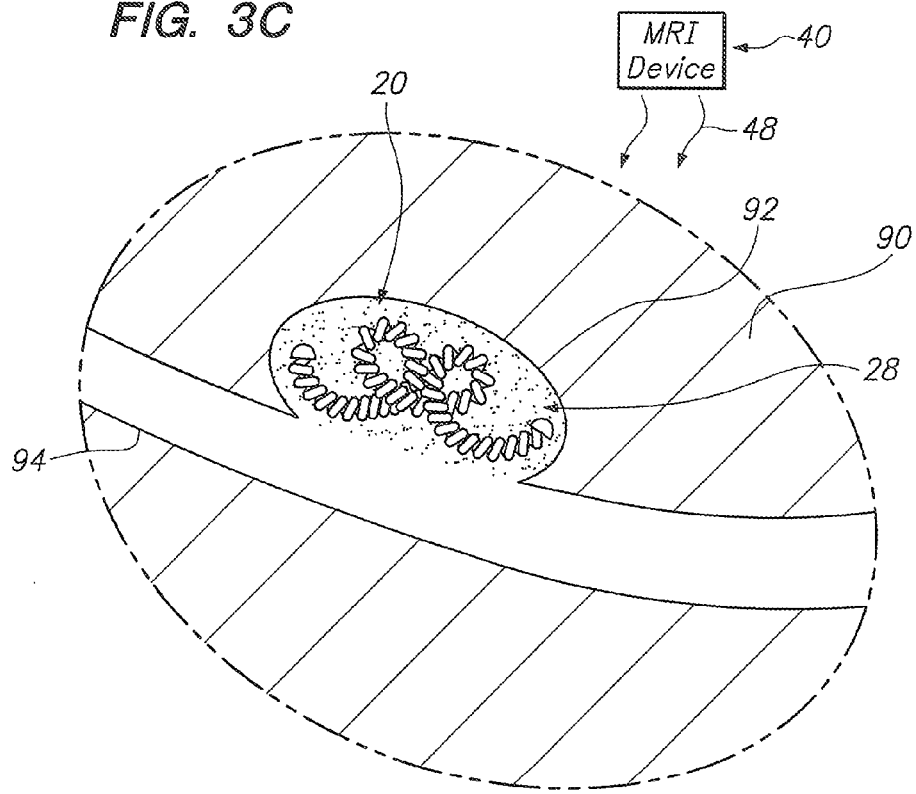

Turning to FIGS. 3A-3C, a method for embolizing and/or occluding an aneurysm 92 is illustrated that employs the system 10 shown in FIG. 1A. In this exemplary method, the vaso-occlusive device 20 may include a bioactive agent, collagenous material, and/or other therapeutic and/or diagnostic agent embedded within or beneath a coating on the coil 22.

Initially, the delivery catheter 30 is introduced into the patient's body 90 from a percutaneous entry site into a peripheral artery, such as the femoral or carotid arteries (not shown), as is well-known. The delivery catheter 30 may be advanced over a guidewire or other rail (not shown) previously placed within the patient's vasculature using known methods. The delivery catheter 30 is advanced through the patient's vasculature, until a distal end 32 of the catheter 30 is disposed within a blood vessel 94 adjacent the aneurysm 92.

Once the catheter 30 is properly positioned, the vaso-occlusive device 20 is advanced through a lumen 34 of the catheter 30 into the aneurysm 92, as shown in FIG. 3A. As the vaso-occlusive device 20 is deployed in the aneurysm, it assume a three-dimensional, deployed configuration. Preferably, the deployed configuration is selected such that the vaso-occlusive device 20 substantially fills the aneurysm 92. Once the vaso-occlusive device 20 is fully deployed within the aneurysm 92, as shown in FIG. 3B, the delivery catheter 30 is removed. Depending on the circumstances (e.g., size and condition of the aneurysm), a treating physician will deploy multiple occlusive devices into a single aneurysm, as is well-known. Additional information on apparatus and methods that may be suitable for delivering the vaso-occlusive coil 20 is found in U.S. Pat. No. 4,994,069 to Ritchart et al., which is incorporated by reference herein for all it teaches and discloses, as well as the other above-incorporated U.S. patents.

Turning to FIG. 3C, once the occlusive coil 22 is implanted and the delivery catheter 30 removed from the body, the MRI machine 40 is activated to at least partially melt or sufficiently soften the coating on the coil 22. This may involve transferring the patient 90 from a catheter lab or other location where the vaso-occlusive device 20 was implanted into a MRI MOM.

As explained above, once the patient 90 is disposed within the MRI magnet 42, the gradient field amplifier 44 (not shown in FIG. 3C, see FIG. 1A) is activated to generate magnetic energy (represented by arrows 48 in FIG. 3C), which interacts with ferrous material in the coil 22 and/or coating to heat the vaso-occlusive device 20. Generally, the MRI machine 40 is activated for a predetermined time, e.g., between about 3 seconds to 20 minutes, to heat the vaso-occlusive device 20 and/or coating to a desired temperature. For example, the vaso-occlusive device and/or coating may be heated to a temperature of at least about 150° F. (about 40° C.).

As the coating reaches its "$T_m$" and/or "$T_g$," the coating may melt and/or flow, thereby releasing or otherwise activating one or more diagnostic or therapeutic agent(s) 28 carried in or beneath the coating. For example, the coating may include a thrombogenic agent that enhances embolization of blood when released within the aneurysm 92. In addition or alternatively, the coating may include one or more agents that remain substantially inert until heated above a predetermined activation temperature. Further additionally or alternatively, the MRI machine 40 may be activated for the to heat the vaso-occlusive device 20 in order to heat blood or other material within the aneurysm 92 and/or tissue surrounding the aneurysm 92, even in the absence of such agent(s). Such heating may accelerate coagulation of blood or other fluid within the aneurysm 92 and/or may cause the surrounding tissue to contract, e.g., to reduce the size of the aneurysm 92, and promote an improved long term healing response.

In accordance with a further aspect of the invention, in an alternate embodiment, at least a portion of the vaso-occlusive device 20 is formed from a material that melts or is otherwise sufficiently softened when heated. In this embodiment, the MRI machine 40 is activated for sufficient time to cause at least a portion of a coating and/or coil of the vaso-occlusive device 20 to melt and/or flow together. When the MRI machine 40 is deactivated, the coil cools, and substantially solidifies, thereby fusing together melted/softened portions of the vaso-occlusive device 20 in its deployed configuration in the aneurysm 92. This fusion stabilizes the vaso-occlusive device 20 in its deployed configuration, helping prevent the device from moving back towards a delivery and/or other generally linear shape.

Figure 4A:
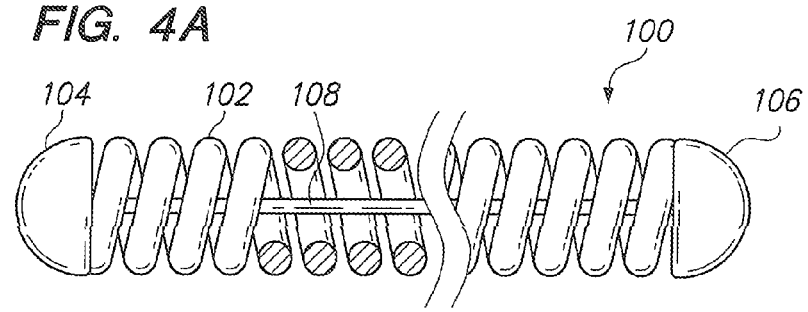
FIGS. 4A and 4B are partial cross-sectional views of further exemplary embodiments of vaso-occlusive devices constructed in accordance with a further aspect of the invention.
Figure 4B:
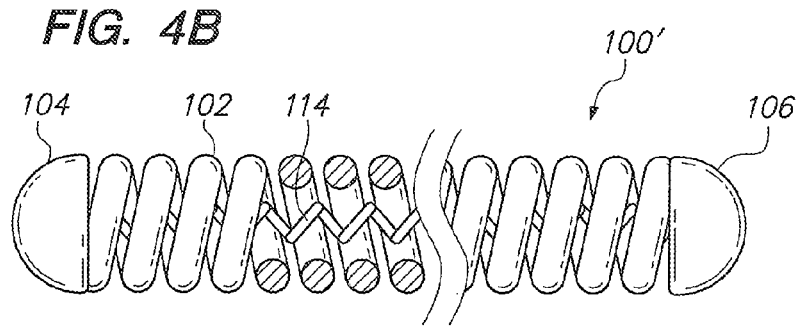

FIGS. 4A and 4B are partial cross-sections (or cutaways) of further embodiments of MR-activated, embolic implant devices 100 and 100', respectively, constructed in accordance with a further aspect of the present invention. The devices 100 and 100' are each made up of a helically wound occlusive coil 102 having a first end 104 and a second end 106. While the coil 102 is depicted in FIGS. 4A and 4B as made from a round wire, i.e., having a substantially circular cross-section, the coil 102 may alternatively be made from a differently shaped wire, e.g., a flat wire having a rectangular cross-section. The coil 102 is preferably made of platinum, and may be provided with a heat-releasable and/or activated agent coating (not shown), as discussed above. Additionally or alternately, a heat-releasable and/or activated agent coating may be provided on the filament 108, 114.

The coil 102 forms a central lumen, through which a ferrous material filament 108 (FIG. 4A), 114 (FIG. 4B) is located, the filament being fixed to the respective first and second ends 104 and 106 of the coil 102. In this manner, the filament 108, 114 acts as a heating element upon application of an AC magnetic field by an MRI machine, as discussed above. In particular, the highly conductive (preferably platinum) coil 102 generates a corresponding highly efficient induction field, which heats the highly resistive ferrous material filament 108, 114 in the coil lumen. Thermal energy in the heated filament is then transferred by convection to the coil 102 and surrounding blood pool and tissue, which has the benefits/effects previously described.

Further additionally or alternately, at least a portion of the coil 102 may be formed from a material that melts or substantially softens when heated, as described above. In this case, fusing points of the coil 102 in its deployed configuration may be determined by locations that the ferrous filament is attached, since these attachment points on the coil 102 will heat the most. It will be appreciated from the present disclosure that the features of a heat-releasable and/or activated agent and structural fusing of the occlusive coil may be provided separately or together in a single, implantable device.

The filament 108, 114 may also (optionally) serve as a stretch resisting member, as taught, for example, in U.S. Pat. No. 5,853,418, which is fully incorporated by reference herein for all that it teaches and discloses. In certain circumstances, it may be desirable to attach the filament 108, 114 only to one of the two ends 104, 106, or alternately (or additionally) to at least one site between the to ends, or to neither of the two ends. Of course, for attaining stretch resistance, if so desired, the filament 108, 114 must be attached to at least two points on the coil 102.

The ferrous filament 108, 114 may be constructed in various ways. For example, the filament 108, 114 may comprise thermoplastic or thermosetting having a bundle of threads or a single filament with one or more metallic ferrous strands formed therein. The filament 108 of the variation shown in FIG. 4A is formed as a ribbon; the filament 114 shown in FIG. 4B is formed as a helically wound coil; in both cases that is soldered, brazed, glued, or otherwise fixedly attached to the first and second coil ends 104 and 106.

In further alternative embodiments, other devices or processes may be employed for in-situ heating of vaso-occlusive devices in accordance with the present invention. For example, an ultrasound device (not shown) may be provided, e.g., including a piezoelectric transducer that may be placed in contact with the patient's skin overlying an aneurysm, lumen, or other cavity where a vaso-occlusive device has been implanted. If desired, an acoustic gel or other material may be provided between the transducer and the patient's skin to enhance acoustically coupling the transducer to the patient, as is known in the art.

Acoustic energy may be delivered from the ultrasound device through the patient's skin and intervening tissue to the cavity to heat the vaso-occlusive device. The energy may be focused or generally directed into the patient's body using known methods. The acoustic energy may be transferred to heat energy when it is absorbed by the vaso-occlusive device and/or surrounding tissue to heat the vaso-occlusive device. The vaso-occlusive device may include materials that enhance acoustic energy absorption and/or attenuation in a predetermined manner to ensure adequate heating of the vaso-occlusive device.

In further alternate embodiments, a source of electrical energy, e.g., a radio frequency ("RF") generator, may be provided adjacent the patient's skin. Electrical energy may be delivered into the patient's body to inductively heat the vaso-occlusive device, as is known to those skilled in the art.

Although the present invention has been described with reference to occlusion and treatment of vasculature sites, such as aneurysms, those skilled in the art will recognize that the methodology of heating an implanted device using an energy source outside of the body could be used for other types of conditions, such as for heating tumors, releasing bioactive agents (e.g., using a low level of heating energy) at any number of intra-body locations, as well as to heat other types of implants, e.g., stents and the like, to enhance patient treatment.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed:

1. A system for embolizing a target site in a vasculature of a body, comprising:
    a vaso-occlusive device detachably coupled to a distal end of a delivery wire insertable through a delivery catheter for deploying the vaso-occlusive device at a target site in a vasculature of a body, wherein the vaso-occlusive device is coated with a therapeutic bioactive agent, and additionally having a polymeric material coating substantially covering the bioactive agent coating; and
    an external energy emitting device configured to deliver energy from a location outside the body to thereby heat the vaso-occlusive device after the vaso-occlusive device has been deployed at the target site in the body, wherein, when heated by energy emitted from the external energy emitting device, the polymeric material coating at least partially melts or softens so that the bioactive agent is released or activated at the target site.

2. The system of claim 1, the target site comprising one of an aneurysm, a blood vessel lumen and a fistula.

3. The system of claim 1, the external energy emitting device comprising a magnetic resonance device.

4. The system of claim 3, wherein the vaso-occlusive device comprises a ferrous material in sufficient concentration to cause heating of the device in response to energy delivered by the magnetic resonance device.

5. The system of claim 1, wherein the external energy emitting device comprises an ultrasound device configured to be acoustically coupled to an exterior surface of the body.

6. The system of claim 1, wherein the external energy emitting device comprises a radio frequency energy generator.

7. A system for embolizing a target site in a body, comprising:
    a vaso-occlusive device detachably coupled to a distal end of a delivery wire insertable through a delivery catheter for deploying the vaso-occlusive device at a target site in a vasculature of a body, the vaso-occlusive device comprising a highly resistive element that is heated by application of a magnetic field, the vaso-occlusive device further comprising a polymeric material exterior coating and a therapeutic bioactive agent underlying the polymeric material coating; and
    a magnetic resonance imaging ("MRI") device, wherein activating the MRI device to apply a variable magnetic field to the body after the vaso-occlusive device has been deployed at the target site heats the highly resistive element in the vaso-occlusive device, thereby at least partially melting or softening the polymeric material exterior coating on the vaso-occlusive device to release or activate the underlying therapeutic bioactive agent.

8. The system of claim 7, wherein the vaso-occlusive device may be sufficiently heated by application of magnetic field energy to cause coagulation of blood at the target site.

9. The system of claim 7, wherein the vaso-occlusive device is configured to assume a three-dimensional shape upon being deployed at the target site, and wherein the vaso-occlusive device may be sufficiently heated by application of magnetic field energy to at least partially melt and fuse together portions of the vaso-occlusive device to thereby stabilize the vaso-occlusive device in the three-dimensional shape.

10. A system for embolizing an aneurysm in a body, comprising:
a vaso-occlusive device detachably coupled to a delivery catheter to thereby deploy the vaso-occlusive device in an aneurysm, the device including:
a highly conductive coil forming a lumen; and
a highly resistive element at least partially disposed in the coil lumen,
wherein the coil is coated with a therapeutic bioactive agent, and additionally
coated with a polymeric material substantially covering the bioactive agent, such that applying magnetic field energy to the device from an energy emitting element located outside of the body would thereby heat the highly resistive element and, by way of convective heat transfer from the highly resistive element, heat the coil to thereby at least partially melt or soften the polymeric material coating to release or activate the bioactive agent.

11. The system of claim 10, the coil comprising platinum; the highly resistive element comprising ferrous material.

12. The system of claim 10, wherein the vaso-occlusive device may be sufficiently heated by application of energy from a source external to the body to cause coagulation of blood at the target site.

13. The system of claim 10, wherein the vaso-occlusive device is configured to assume a three-dimensional shape upon being deployed at the target site, and wherein the vaso-occlusive device may be sufficiently heated by application of energy from a source external to the body to at least partially melt and fuse together portions of the vaso-occlusive device to thereby stabilize the vaso-occlusive device in the three-dimensional shape.

* * * * *